United States Patent [19]

Craig, Jr. et al.

[11] 4,091,005
[45] May 23, 1978

[54] CONTINUOUS PROCESS FOR PREPARATION OF ISOPROPENYL STEARATE

[75] Inventors: James C. Craig, Jr., Maple Glen; Michael F. Kozempel, Warminster, both of Pa.

[73] Assignee: The United States of America as represented by the Secretary of Agriculture, Washington, D.C.

[21] Appl. No.: 729,443

[22] Filed: Oct. 4, 1976

[51] Int. Cl.² .............................................. C11C 3/02
[52] U.S. Cl. ............................................ 260/410.9 N
[58] Field of Search ................................ 260/410.9 N

[56] References Cited

U.S. PATENT DOCUMENTS

| | | | |
|---|---|---|---|
| 2,472,086 | 6/1949 | Beller et al. | 260/410.9 N |
| 3,607,915 | 9/1971 | Borsboom et al. | 260/410.9 N |
| 3,646,077 | 2/1972 | Hubner et al. | 260/410.9 N |
| 3,666,781 | 5/1972 | Serota et al. | 260/410.9 N |
| 3,878,230 | 4/1975 | Rothman et al. | 260/410.9 N |
| 3,898,252 | 8/1975 | Serota et al. | 260/410.9 N |

*Primary Examiner*—Winston A. Douglas
*Assistant Examiner*—John F. Niebling
*Attorney, Agent, or Firm*—M. Howard Silverstein; William E. Scott; David G. McConnell

[57] ABSTRACT

A continuous process for the preparation of isopropenyl stearate in which a comelt of stearic acid and zinc stearate is pumped through a reaction zone simultaneously with stabilized propyne. Total reaction time is about 10 minutes.

8 Claims, 1 Drawing Figure

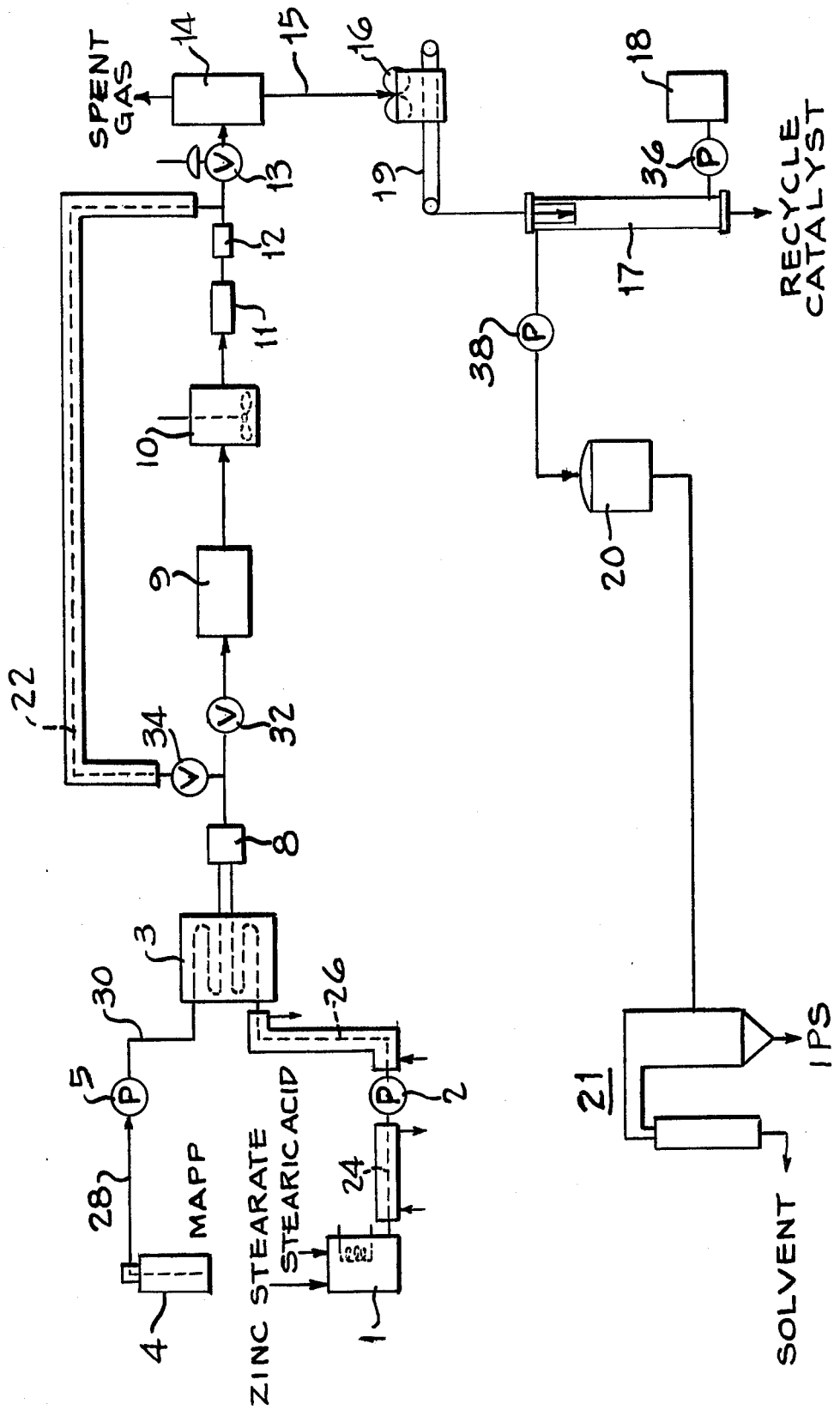

CONTINUOUS PROCESS FOR PREPARATION OF ISOPROPENYL STEARATE

BACKGROUND OF THE INVENTION

1. Field of the Invention

This invention pertains to the production of isopropenyl stearate and more particularly to an integrated continuous process for producing isopropenyl stearate.

2. Description of the Prior Art

U.S. Pat. Nos. 3,666,781, 3,878,230, and 3,898,252 describe the preparation of enol esters including isopropenyl stearate. However, the processes described by these patents are all batch type reaction processes that are neither continuous nor adaptable to a continuous reaction. As batch processes they all require hours of reaction time to obtain the desired product.

SUMMARY OF THE INVENTION

The object of this invention is to provide an integrated continuous process for the preparation of isopropenyl stearate and other enol esters in which the total reaction time is about ten minutes or less.

According to the present invention, the above object is accomplished by a process in which a comelt of stearic acid and zinc stearate catalyst is reacted continuously with propyne or with a stabilized propyne. The reactants are simultaneously and continuously pumped into and through a reaction zone wherein the total residence time of the reactants is about ten minutes or less. Spent reaction gas is flashed off, the product is crystallized on chilled flaker rolls, the crystallized product is leached to remove catalyst, and solvent is then removed by stripping.

BRIEF DESCRIPTION OF THE DRAWING

FIG. 1 is a schematic outline of the continuous integrated process of this invention.

DETAILED DESCRIPTION OF THE INVENTION

The stabilized propyne used in this invention is known as MAPP gas. It is a mixture containing approximately 65% methylacetylene-propadiene with the balance made up of saturated and unsaturated $C_3$ and $C_4$ hydrocarbons to stabilize the mixture and to insure that the concentration of methylacetylene-propadiene remains nearly constant at all times during the vaporization of the mixture. A further description and discussion of MAPP gas and its physical properties is found in Welding Journal, 3-9, (February 1966).

Explosion proof construction was used throughout the process. Components 8 through 12 in the reaction zone, as well as heat exchanger 3 and components 13 and 14, were enclosed in a barricade for safety. Prior to starting the reaction, oleic acid, which was heated in a tank not shown in FIG. 1, was piped to the suction side of gear pump 2 and then pumped through the system to warm heat sinks. Steam-jacketed line 22 and valves 32 and 34 were provided to bypass components 9 through 12 in the reaction zone during start-up and shutdown.

Stearic acid and zinc stearate catalyst were comelted and agitated in glass lined kettle 1. The comelt was then conveyed through double pipe heat exchanger 24 to the suction side of gear pump 2, from which it was pumped through another double pipe heat exchanger 26 which went through shell and tube heat exchanger 3 before entering the reaction zone. Cylinder 4 containing MAPP gas was fitted with siphon tubes 28 to permit feeding the gas as a liquid to diaphragm pump 5 from where it was pumped through conduit 30 which also went through shell and tube heat exchanger 3 before entering the reaction zone. Heat exchanger 3 was provided with thermal fluid on the shell.

The reaction zone consisted of mixing chamber 8, plug flow reactor 9, continuous stirred tank reactor 10, and two finishing plug flow reactors 11 and 12. Although two finishing plug flow reactors were used, there appears to be no reason why one would not be sufficient. The reaction began in mixing chamber 8 where the MAPP gas and the liquid stream of comelt were intimately mixed. The reaction continued in plug flow reactor 9, and then as the reaction mixture flowed through the apparatus, the bulk of the reaction took place in the continuous stirred tank reactor 10, and was finished in the two finishing plug flow reactors 11 and 12. Pressure control valve 13 was used to control the pressure in the reactor. The flow of reactants into the continuous stirred tank reactor, which was operated full at all times, entered at the bottom and exited at the top. This eliminated the problem of an unmeasurable void volume which was encountered in a modified batch reactor.

When the reaction was completed, spent MAPP gas was removed from the product mixture in flash chamber 14. Gases were vented overhead and a liquid seal (not shown) was maintained at the bottom drain 15 to prevent leakage of spent gases into the atmosphere. A sight glass was provided in the barricade to permit remote manual control of the liquid level in chamber 14. Liquid exiting from the flash chamber was at a temperature of about 280° F and contained no apparent dissolved gas. Since isopropenyl stearate reacts slowly with stearic acid to form stearic anhydride the reaction was quenched by rapidly solidifying the product on double drum flaker 16. Drum clearance was 0.044 inches and the drums were cooled by circulating water at a temperature of about 50° F at a rate of about 2.9 gallons per minute. The product, an amorphous solid, was scraped from the drums with doctor blades.

The recovery system consisted of three unit operations: leaching, filtration, and evaporation. Reaction product was fed to the top of leaching column 17 by dry chemical feeder 19, and solvent from reservoir 18 was fed by pump 36 into the bottom of column 17. Skellysolve B, a normal hexane-type solvent with a boiling point range of 63° to 70° C, was used as the leaching solvent. The supernatant, fed by pump 38, was clarified in a horizontal plate and frame filter (Sparkler) 20 and the solvent removed from the product in solvent stripper 21.

There are several critical conditions that must be met for the process of this invention to operate efficiently. For example, optimum reaction conditions require a zinc stearic catalyst/stearic acid ratio of 52/48 by weight, a pressure of 550 psi, a temperature of 415° F plus or minus 5° F, MAPP gas containing 30% or more propyne, and a molar ratio of propyne to stearic acid of at least 0.9. A residence time of 9 to 9.5 minutes in the reaction zone, including 0.6 minutes in the finishing plug flow reactor, is essential to obtaining a good yield of product. Treatment of the exit stream from the flash chamber is also important. Rapid chilling of the exit stream produced from an initial feed containing 52% zinc stearate, that is, a zinc stearate/stearic acid ratio of 52/48, yields a product that resembles damp soap flakes and is easily leached. Slow chilling of an identical exit stream produces a slurry that is difficult to leach. Rapid chilling of an exit stream produced from an initial feed containing less than 52% zinc stearate yields a product that resembles wet soap flakes and is difficult to leach. Consequently, in order for the leaching process to operate most efficiently, the initial feed to the process should contain at least 52% zinc stearate and the exit stream from flash tank 14 should be continuous and should be chilled rapidly.

MAPP gas was used in the process of this invention because it is relatively inexpensive and is known to be safe. However, we found equilibrium conversion to be a function of the propyne concentration in MAPP gas. Larger yields of product were obtained when the MAPP gas contained higher percentages of propyne. Although MAPP gas was used for cost and safety reasons, there is no reason to believe that purified propyne could not be used in its place.

As seen in FIG. 1, catalyst recovered from leaching column 17 can be recycled.

The following is an example of a typical run:

Stearic acid (46.15 lb) and zinc stearate (50.0 lb) were charged to kettle 1. Thermal fluid for heat exchange was heated to 400° F. Oleic acid, which had been preheated, was pumped through the system using bypass 22 to exclude components 9 through 12. After several minutes, the feed was switched from oleic acid to the stearic acid-zinc stearate feed. One minute later MAPP gas from cylinder 4 was pumped at 4.2 lb/hr. Another minute later the process stream was switched from bypass 22 to components 9–12. When the temperature in the reaction zone stabilized, the reactor pressure was increased to 550 psig and restabilized in about 5 minutes (14 minutes total time from the start of the stearic acid feed).

Spent MAPP gas was automatically vented from the flash chamber 14 so as to maintain a pressure of about 25 psig. A liquid seal was maintained at the bottom of the flash chamber by a manually, remotely operated valve on drain 15.

The liquid level in the flash chamber was observed through a view port in the barricade. The liquid dropped directly onto the flaker, solidified, and was doctored off at the rate of 20.3 lb/hr. The product was manually removed from a trough beneath the flaker. Access was provided by a slit in the barricade wall.

In order to be certain that the reactor had reached steady state, product was sent via dry feeder 19 to leaching column 17 about 40 minutes after the start of the stearic acid-zinc stearate feed. Simultaneously with the start of dry feeder 19, solvent was pumped into the previously solvent filled leaching column 17 at 0.6 gal/min. The solids were fed at 0.26 lb/min.

The supernatant was collected in a reservoir and pumped to Sparkler filter 20. The filtrate was collected and stored. Solvent was stripped from the isopropenyl stearate in solvent stripper 21. The product was analyzed as 91.5% isopropenyl stearate.

Although the process of this invention has been exemplified with stearic acid there is no reason that other fatty acids from vegetable and animal sources could not be substituted for the stearic acid even though they may require process parameters to be modified. Solvents such as acetone, butanol, methanol, carbon disulfide, and chloroform may be used for leaching in place of Skellysolve B. In addition, other methods of recovery such as evaporation and extraction may also be used.

We claim:

1. A process for the preparation of isopropenyl stearate comprising the steps of:
   (a) reacting stearic acid and propyne by simultaneously and continuously pumping stablizied propyne and a comelt of stearic acid and zinc stearate into and through a reaction zone, the molar ratio of propyne to stearic acid being at least 0.9, the stearic acid and zinc stearate being present in said comelt at a ratio of 48:52 by weight and said mixture reacting at about 410° to 420° F under 550 psig.;
   (b) flashing off spent reaction gas;
   (c) crystallizing the product on chilled flaker rolls;
   (d) leaching the crystallized product to remove catalyst; and
   (e) removing the solvent from the product.

2. The process of claim 1 in which the stabilized propyne contains at least 30% propyne.

3. An integrated, continuous process for preparing isopropenyl stearate, comprising the steps of:
   (a) comelting 48 parts by weight of stearic acid with 52 parts by weight of zinc stearate;
   (b) initiating a reaction of stearic acid and propyne by pumping simultaneously and continuously through a mixing chamber and a plug flow reactor preheated comelt of step (a) and preheated stabilized propyne, the molar ratio of propyne to stearic acid being at least 0.9;
   (c) completing the bulk of the reaction initiated in step (b) by pumping the reaction mixture through a constant stirred tank reactor, said mixture reacting at about 410° to 420° F under 550 psig., the residence time of said mixture in said reactor being about 9 to 9.5 minutes;
   (d) finishing the reaction by pumping the product of step (c) through a plug flow reactor, the residence time of said product in said reactor being at least 0.6 minutes;
   (e) flashing off spent stabilized propyne gas;
   (f) crystallizing the product of the reaction on chilled flaker rolls;
   (g) leaching the product to remove zinc catalyst;
   (h) removing the solvent to obtain the product.

4. In a process for preparing isopropenyl stearate wherein stabilized propyne is reacted with a comelt of stearic acid and zinc stearate, the improvement wherein the comelt and stabilized propyne are reacted continuously while being pumped through a reaction zone, the total residence time in said reaction zone being about 10 minutes and the ratio of stearic acid to zinc stearate in the comelt being 48:52 by weight.

5. The improvement of claim 4 wherein the stabilized propyne contais at least 30% propyne.

6. The improvement of claim 5 wherein the molar ratio of propyne to stearic acid is at least 0.9.

7. The improvement of claim 6 wherein the reaction zone consists of a mixing chamber, a plug flow reactor, a constant stirred tank reactor, and a finishing plug flow reactor.

8. The improvement of claim 7 wherein the bulk of the reaction takes place in the constant stirred tank reactor during a residence time of about 9 to 9.5 minutes at a temperature of about 410° to 420° F under 550 psig.

* * * * *